(12) United States Patent
Keifer

(10) Patent No.: US 6,855,667 B2
(45) Date of Patent: Feb. 15, 2005

US006855667B2

(54) METHOD FOR SAFENING CROPS FROM THE PHYTOTOXIC EFFECTS OF HERBICIDES BY USE OF PHOSPHORATED ESTERS

(75) Inventor: David W. Keifer, Hopewell, NJ (US)

(73) Assignee: FMC Corporation, Philadelphia, PA (US)

( * ) Notice: Subject to any disclaimer, the term of this patent is extended or adjusted under 35 U.S.C. 154(b) by 75 days.

(21) Appl. No.: 10/181,231

(22) PCT Filed: Jan. 5, 2001

(86) PCT No.: PCT/US01/00219
§ 371 (c)(1),
(2), (4) Date: Nov. 13, 2002

(87) PCT Pub. No.: WO01/50858
PCT Pub. Date: Jul. 19, 2001

(65) Prior Publication Data
US 2005/0009702 A1 Jan. 13, 2005

Related U.S. Application Data

(60) Provisional application No. 60/176,340, filed on Jan. 14, 2000.

(51) Int. Cl.[7] .......................... A01N 25/32; A01N 43/90
(52) U.S. Cl. ...................... 504/103; 504/104; 504/105; 504/106; 504/107; 504/110; 504/111; 504/112; 504/241
(58) Field of Search .............................. 504/103, 104, 504/105–112, 241; 552/203, 204, 205; 540/120; 544/14; 514/31, 152, 153, 154, 222.2

(56) References Cited

U.S. PATENT DOCUMENTS

| | | |
|---|---|---|
| 3,920,442 A | 11/1975 | Albert |
| 4,379,716 A | 4/1983 | Schafer et al. |
| 4,822,401 A | 4/1989 | Tymonko |
| 4,915,725 A * | 4/1990 | Hyzak et al. ............... 504/113 |
| 5,484,760 A * | 1/1996 | Bussler et al. ............... 504/103 |
| 5,880,066 A * | 3/1999 | Wells et al. ................. 504/103 |
| 6,683,027 B2 * | 1/2004 | Baltruschat et al. ........ 504/128 |

FOREIGN PATENT DOCUMENTS

WO 03/051122 * 6/2003

OTHER PUBLICATIONS

Document No. 140:787, HCAPLUS, abstract of WO 2003097095.*
Document No. 139:64821, HCAPLUS, abstract of WO 200305112.*
G.S. Hassawy, et al., "Effects of Trifluralin and Organophosphorus Compounds on Cotton Seedlings," Weed Science, Issue 2, vol. 19, p. 166–169, (Mar., 1971).
H.F. Arle, "Trifluralin–Systemic Insecticide Interactions on Seedling Cotton," Weed Science, vol. 16, p. 430–432, (1968).
D.G. Mosier, et al., "Herbicide—Mode of Action," Cooperative Extension Service, Kansas State University (Manhattan), p. 3–12, (Oct., 1990).

* cited by examiner

Primary Examiner—Sabiha N. Qazi
(74) Attorney, Agent, or Firm—FMC Corporation

(57) ABSTRACT

The present invention relates to protection of plants from unintended phytotoxic injury due to application of a herbicide to reduce competition for the plant of interest. A preferred herbicide used in the context of the present invention is clomazone. The unintended phytotoxic injury is avoided by application of a safening-effective amount of one or more of the compounds described by formula (I) wherein T and $T^1$ are independently selected from the group of hydrogen, alkyl, haloalkyl, alkoxyalkyl, alkenyl, and alkynyl; U is oxygen or sulfur, and; V, W, X, Y, and Z are independently selected from the group of hydrogen, halogen, alkyl, haloalkyl, and alkoxy. The present invention is preferably used for growing corn, wheat, and cotton in the presence of the otherwise phytoxic effects of clomazone, for example.

16 Claims, No Drawings

METHOD FOR SAFENING CROPS FROM THE PHYTOTOXIC EFFECTS OF HERBICIDES BY USE OF PHOSPHORATED ESTERS

This application claims the benefit of Provisional application Ser. No. 60/176,340, filed Jan. 14, 2000.

The present invention generally relates to the field of controlling unwanted plant species, and in particular to methods for safening crops or ornamentals that are subjected to certain herbicides.

Herbicides are useful for controlling unwanted vegetation, i.e., weeds, which may otherwise cause significant damage to desirable plant species such as crop plants or ornamentals. Many potent herbicides have the ability to control for full growing seasons and at low rates of application, a broad spectrum of grass and broadleaf weeds that compete with desirable plants or crops such as wheat, cotton, or corn. Unfortunately, certain potent herbicides are not tolerant, or are phytotoxic, to a wide variety of desirable plants when applied at rates effective to control unwanted vegetation. Measures to increase the tolerance of, or safening sensitive crops to certain herbicides without substantial diminution of herbicidal efficacy, would greatly expand the usefulness of these herbicides.

One approach to increasing the tolerance of sensitive crops to certain herbicides while maintaining broad spectrum weed control is through the use of genetically-modified crop seed lines that have tolerance to the otherwise phytotoxic herbicide. Unfortunately, high technology costs, as well as the discomfort of many consumers to the introduction of such genetically modified crops to the market, has rendered this solution of increasing the tolerance of crops to be inadequate.

Another approach to increasing the tolerance of sensitive crops is through the use of "safener" compounds in conjunction with applications of the phytotoxic herbicide. For example, certain gramineous crops are safened from the phytotoxic effects of the herbicide sulfentrazone with the use of crop-safening amounts of 1,8-naphthalic anhydride. In addition, certain cereal crops and cotton are safened from the phytotoxic effects of the herbicide clomazone with the use of crop-safening amounts of organophosphorus compounds related to the insecticides phorate, disulfoton, terbufos, dimeton, and dimethoate. The use of insecticidal organophosphorus compounds has been banned in some countries, however, and is under increased scrutiny from government regulatory agencies in other countries. It is expected that a world-wide ban of these compounds will be effected in the near future.

An alternative method for safening crops and other valuable or otherwise desirable plants to the phytotoxic effects of herbicides in agriculture would provide another useful agronomic tool to farmers, and is needed.

SUMMARY OF THE INVENTION

It has now been found that certain plants crops can be safened, i.e., protected from significant phytotoxic injury, upon application of a herbicidally effective amount of a herbicidal compound when said plants are also treated with a safening-effective amount of one or more safening compounds having formula (I):

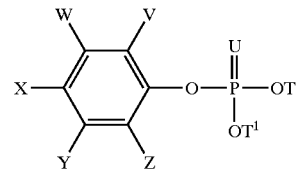

where T, $T^1$, U, V, W, X, Y, and Z are described below. Preferred compounds are those where T, and $T^1$ are independently selected from hydrogen, methyl, ethyl, propyl, and butyl; U is sulphur, and; V, W, X, Y, and Z are independently selected from hydrogen, halogen, and alkyl. The plant-safening compounds having formula (I) are preferably pesticidally non-toxic phosphorated esters that have no or little effect on environmental flora or fauna at rates of application set forth herein. Agricultural chemical compositions and methods of applying these compositions to the locus where desirable plants are growing or are expected to grow are among the preferred embodiments of the present invention.

Definitions

The modifier "about" is used herein to indicate that certain preferred operating ranges, such as ranges for rates of application of herbicides to the locus where herbicidal control is desired, are not fixedly determined. The meaning will often be apparent to one of ordinary skill. For example, a recitation of a rate of application of herbicide of about 0.001 kg/ha to about 15 kg/ha would be interpreted to include other like rates of application of herbicide that can be expected to favor control of weed species, such as, for example, 0.0005 kg/ha and 18 kg/ha. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

As used in this specification and unless otherwise indicated, the substituent terms alkyl, alkenyl, alkynyl, alkoxy, and haloalkyl, used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. "Halogen" or "halo" refers to fluorine, bromine, iodine, or chlorine.

As used herein, the terms "crop", "crops", "plant" or "plants" are one and the same, and refer to plants of interest or plant products derived thereof that are grown for ornamental, industrial or food uses. The term "seed" or "seeds" refers to the grains or ripened ovules used to produce a new crop, crops, plant, or plants. The term "phytotoxic injury" as used herein means unintended herbicidal effect on a plant of interest resulting in significant damage to the plant. The term "weed" refers to an unwanted plant that is growing in a place or in a manner that is detrimental to a plant of interest. The term "safening" refers to the protection of a plant of interest from significant phytotoxic injury due to herbicide treatment, while the term "safener" refers to a chemical compound, or the like, with the ability to afford that protection. The term "injury" in the context of the present invention relates to stunting and/or discoloration of plants. The term "percent injury" as it relates to an assessment of the phytotoxic damage caused to plants by a herbicidal compound refers to the amount of damage, or injury, to plants in comparison to the damage caused to the total, or the whole number of plants. The term "percent reduction of injury" refers to a comparison of the percent injury to safened plants as compared to the percent injury to unsafened plants.

DETAILED DESCRIPTION OF THE INVENTION

The present invention relates to a method of protecting a plant from unintentional phytotoxic injury from application of a herbicidally-effective amount of a herbicidal compound to the locus of the plant, which method comprises applying to said locus an effective amount of one or more safening compounds having formula (I):

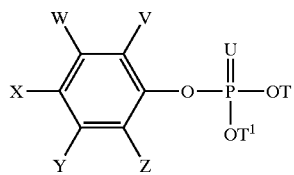

where:
T and $T^1$ are independently selected from the group of hydrogen, alkyl, haloalkyl, alkoxyalkyl, alkenyl, and alkynyl;
U is oxygen or sulfur, and;
V, W, X, Y, and Z are independently selected from the group of hydrogen, halogen, alkyl, haloalkyl, and alkoxy.

As set forth herein, there are many herbicides (termed hereinafter as "herbicidal compound or compounds") with varying degrees of selectivity and phtotoxicity to both weeds and crops alike that could provide added utility if they were safened to a broader range of crops. The herbicidal compound or compounds include, without limitation, N-(phosphonomethyl)glycine (glyphosate) and its alkali metal salts, alkaline earth metal salts, ammonium salts, organic amine salts, and its sulfonium salts; herbicides derived from an aryloxyalkanoic acid, for example, (2,4-dichlorophenoxy)acetic acid (2,4-D), (4-chloro-2-methylphenoxy)acetic acid (MCPA), or (+/−)-2-(4chloro-2-methylphenoxy)propanoic acid ("MCPP"); herbicides derived from a urea, for example, N,N-dimethyl-N'-[4-(1-methylethyl)phenyl]urea (isoproturon); herbicides derived from an imidazolinone, for example, 2-[4,5-dihydro-4-methyl-4-(1-methylethyl)-5-oxo-1H-imidazol-2-yl]-3-pyridinecarboxylic acid (imazapyr); herbicides derived from a benzoic acid, for example, (+/−)-2-[4,5-dihydro-4-methyl-4-(1-methylethyl)-5-oxo-1H-imidazol-2-yl]-4-methylbenzoic acid and (+/−)2-[4,5-dihydro-4-methyl-4-(1-methylethyl)-5-oxo-1H-imidazol-2-yl]-5-methylbenzoic acid (imazamethabenz); herbicides derived from a carboxylic acid, for example, (+/−)-2-[4,5-dihydro-4-methyl-4-(1-methylethyl)-5-oxo-1H-imidazol-2-yl]-5-ethyl-3-pyridinecarboxylic acid (imazethapyr), and (+/−)-2-[4,5-dihydro-4-methyl-4-(1-methylethyl)-5-oxo-1H-imidazol-2-yl]-3-quinolinecarboxylic acid (imazaquin); herbicides derived from a diphenyl ether, for example, 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); herbicides derived from a hydroxybenzonitrile, for example, 4-hydroxy-3,5-diiodobenzonitrile (ioxynil) and 3,5-dibromo-4-hydroxybenzonitrile (bromoxynil); herbicides derived from a sulfonylurea, for example, 2-[[[[(4chloro-6-methoxy-2-pyrimidinyl)amino]carbonyl]amino]sulfonyl]benzoic acid (chlorimuron), 2-chloro-N-[[(4-methoxy-6-methyl-1,3,5-triazin-2-yl)amino]carbonyl]benzenesulfonamide (chlorsulfuron), 2-[[[[(4,6-dimethoxy-2-pyrimidinyl)-amino]carbonyl]amino]sufonyl]methyl]benzoic acid (bensulfuron), 2-[[[[(4,6-dimethoxy-2-pyrimidinyl)amino]carbonyl]amino]sulfonyl]-1-methyl-1H-pyrazol-4-carboxylic acid (pyrazosulfuron), 3-[[[[(4-methoxy-6-methyl-1,3,5-triazin-2-yl)amino]carbonyl]amino]sulfonyl]-2-thiophenecarboxylic acid (thifensulfuron), and 2-(2-chloroethoxy)-N[[(4-methoxy-6-methyl-1,3,5-triazin-2-yl)amino]carbonyl]benzenesulfonamide (triasulfuron); herbicides derived from a 2-(4-aryloxyphenoxy)alkanoic acid, for example, (+/−)-2[4-[(6-chloro-2-benzoxazolyl)oxy]phenoxy]propanoic acid (fenoxaprop), (+/−)-2-[4-[[5-(trifluoromethyl)-2-pyridinyl]oxy]phenoxy]propanoic acid (fluazifop), (+/−)-2-[4-(6chloro-2-quinoxalinyl)oxy]phenoxy]propanoic acid (quizalofop), and (+/−)-2-[(2,4-dichlorophenoxy)phenoxy]propanoic acid (diclofop); herbicides derived from a benzothiadiazinone, for example, 3-(1-methylethyl)-1H-2,1,3-benzothiadiazin-4(3H)-one-2,2-dioxide (bentazone); herbicides derived from a 2-chloroacetanilide, for example, N-(butoxymethyl)-2-chloro-2',6'-diethyacetanilide (butachlor), 2-chloro-N-(2,6-diethylphenyl)-N-(methoxymethyl)acetamide (alachlor), (RS)-2-chloro-N-(2,4-dimethyl-3-thienyl)-N-(2-methoxy-1-methylethyl)acetamide (dimethenamide), and 2-chloro-N-(2-ethyl-6-methylphenyl)-N-(2-methoxy-1-methylethyl)acetamide (metolachlor); herbicides derived from an arenecarboxylic acid, for example, 3,6-dichloro-2-methoxybenzoic acid (dicamba); herbicides derived from a thiocarbamate, for example, S-ethyl hexahydro-1H-azepine-1-carbothioate (molinate), and S-ethyl dipropylcarbamothioate (EPTC); herbicides derived from a dinitroaniline, for example, 2,6-dinitro-N,N-dipropyl-4-(trifluoromethyl)benzenamine (trifluralin), and N-(1-ethylpropyl)-3,4-dimethyl-2,6-dinitrobenzenamine (pendimethalin); herbicides derived from a triazine, for example, 4-amino-6-(1,1-dimethylethyl)-3-(methylthio)-1,2,4-triazin-5-one (metribuzin), and 6-chloro-N-ethyl-N'-(1-methylethyl)-1,3,5-triazine-2,4-diamine (atrazine); herbicides derived from a bipyridyl, for example, 1,1'-dimethyl-4,4"-bipyridinium (paraquat); herbicides derived from a 3-isoxazolidinone, for example, 2-[(2-chlorophenyl)methyl]-4,4-dimethyl-3-isoxazolidinone (clomazone); herbicides derived from a triazolinone, for example, N-[2,4-dichloro-5-[(4-difluoromethyl)4,5-dihydro-3-methyl-5-oxo-1H-1,2,4-triazol-1-yl]phenyl]methanesulfonamide (sulfentrazone), and ethyl α-2-dichloro-5-[4-(difluoromethyl)-4,5-dihydro-3-methyl-5-oxo-1H-1,2,4-triazol-1-yl]-4-fluorobenzenepropanoate (carfentrazone ethyl); herbicides derived from a pyridyloxyacetic acid, for example, [(4-amino-3,5-dichloro-6-fluoro-2-pyridinyl)oxy]acetic acid (fluroxypyr); herbicides derived from a cyclohexene, for example, (+/−)-2-[1-(ethoxyimino)butyl]-5-[2-(ethylthio)propyl]-3-hydroxy-2-cyclohexen-1-one (sethoxydim), and (E,E)-(+/−)-2-[1-[[3-chloro-2-propenyl)oxy]imino]propyl]-5-[2-(ethylthio)propyl]-3-hydroxy-2-cyclohexen-1-one (clethodim), and other herbicides, for example, (+/−)-2-amino-4-(hydroxymethylphosphinyl)butanoic acid (glufosinate), N-(2,4-difluorophenyl)-2-(trifluoromethyl)phenoxy]-3-pyridinecarboxamide (diflufenican), and (5-cyclopropylisoxazol-4-yl)(2-methylsulfonyl-4-trifluoromethylphenyl)ketone (isoxaflutole).

A preferred species of herbicidal compound for safening in the context of the present invention is derived from 3-isoxazolidinones having formula (II):

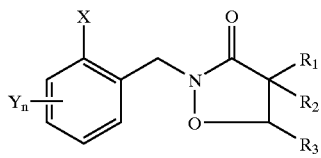

(II)

where:
- $R_1$ and $R_2$ are independently selected from $C_1$–$C_4$ alkyl;
- $R_3$ is hydrogen, halogen, phenylamino, or —$OR_4$ in which $R_4$ is hydrogen, lower alky, alkenyl, alkynyl, alkoxyalkyl up to 6 carbons, phenylmethyl, $C_2$–$C_4$ acyl, haloacyl, phenylacyl, alkylcarbonylamino, or phenylcarbonylamino;
- X is hydrogen, lower alky, or halogen;
- Y is halogen, cyano, $C_1$–$C_4$ alkoxy, or 4,5-methylenedioxy, and;
- n is 0, 1, or 2.

More preferred herbicidal compound or compounds having formula (II) are those wherein $R_1$ and $R_2$ are independently methyl or ethyl; X is chlorine, bromine, or fluorine; when n is 1, Y is either (1) chlorine or fluorine in the 4- or 5-position, or (2) bromine in the 4-position; when n is 2, Y is either (1) chlorine in the 4- and 5-position or (2) fluorine in the 4- and 5-position. The most preferred herbicidal compound having formula (II) is that wherein $R_1$ and $R_2$ are methyl, $R_3$ is hydrogen, X is chlorine, and n is 0, which herbicidal compound is commonly known as clomazone.

More preferred species of a safening compound of formula (1) are those wherein T and $T^1$ are independently selected from hydrogen, methyl, ethyl, propyl, and butyl; U is sulfur, and; V, W, X, Y, and Z are independently selected from hydrogen, halogen, and alkyl. The most preferred species of a safening compound of formula (I) is that where T and $T^1$ are ethyl, U is sulfur, and; V, W, X, Y, and Z are hydrogen, which safening compound is commonly known as dietholate.

Plants of interest that can be safened in the context of the present invention preferably include, without limitation, soybean, cotton, sugarbeet, rape (canola), potato, sunflower, peanut, lettuce, carrot, sweet potato, alfalfa, tobacco, corn (maize), rice, sorghum, wheat, barley, oats, rye, triticale, and sugarcane. More preferred plants on which to apply the compounds or the compositions of the present invention are soybean, wheat, corn, cotton, sugarbeet, rape, potato, sunflower, peanut, lettuce, carrot, sweet potato, alfalfa, and tobacco. The most preferred plants to which the present invention is applied are wheat, corn, and cotton, especially cotton.

In methods of applying the compounds or compositions of the present invention where herbicidal activity and increased tolerance, or safening of plants is desired, a herbicidal compound (U) is applied to the locus of the plant, or to the locus of where the plant is to be planted in the amount of from about 0.001 to about 15 kilograms/hectare and a safening compound (I) is applied to the same locus in an amount of from about 0.003 to about 15 kilograms/hectare. At the lower concentrations of application, the safening compound generally has no phytotoxic effect; however, at the higher concentrations, the safening compound can itself be phytotoxic, but preferably not to plants of interest. More preferably, the amount of the herbicidal compound is about 0.003 to about 5 kilograms/hectare and the amount of the safening compound is about 0.01 to about 5 kilograms/hectare. Most preferably, the amount of the herbicidal compound is about 0.01 to about 2 kilograms/hectare and the amount of the safening compound is about 0.03 to about 2 kilograms/hectare.

In the context of the present invention, methods of application of the herbicidal compound and the safening compound include those wherein the herbicidal compound is applied to a locus of the plant, or to a locus of where the plant is to be planted, independently with respect to application of the safening compound.

In one embodiment, the herbicidal compound can be applied prior to application of the safening compound. Safening of plants to the phytotoxic effects of the herbicidal compound can result by application of the safening compound up to a few days later, for example, from about three to seven days later. A preferred application of said safening compound would take place up to about a day later, more preferably about six to eight hours later.

In a second embodiment, the safening compound is applied prior to the herbicidal compound. Safening of plants as described hereinabove occurs when the herbicidal compound is applied up to about four weeks later than the application of the safening compound. A preferred application of the herbicidal compound would take place up to about four days later, more preferably about one to two days later.

In a third embodiment, the herbicidal compound is preferably applied in admixture with the safening compound. When the herbicidal compound is applied in admixture with the safening compound, the individual compounds are mixed together and applied in one application to the locus of the plant, or to a locus of where the plant is to be planted. An effective admixture of herbicidal compound and safening compound is prepared independent of the order in which the compounds are combined, and can be prepared at any time prior to application of the admixture. Preferably, the mixture of compounds is applied as a tank mix wherein the admixture is prepared immediately prior to the time of application to said locus.

In a fourth embodiment, the safening compound is applied as a seed treatment of plant seeds. The herbicidal compound can be applied independently with respect to the planting of the treated seed. That is to say, the treated seeds can be planted prior to, subsequent to, or simultaneously with the application of the herbicidal compound. Depending upon the compound being used as a seed treatment and the plant seed being treated, the seed treatment can be applied to the seed in any safening-effective amount and at any time prior to the planting of the seed. In a preferred method, the seed treatment, i.e., the safening compound can be applied to the plant seed immediately prior to the planting of the seeds.

A preferred amount of safening compound applied as a seed treatment to the plant seeds is in the range of from about 0.005 weight percent to about 10 weight percent of the weight of the plant seeds. A more preferred amount of safening compound applied as a seed treatment to the plant seeds is about 0.015 weight percent to about 3 weight percent of the weight of the plant seeds, and most preferred, about 0.05 weight percent to about 1 weight percent.

The present invention also relates to herbicidally active agricultural chemical compositions that combine the compounds of the present invention with adjuvants and carriers normally employed in the art for facilitating the dispersion of active ingredients for the particular utility desired. One skilled in the art will, of course, recognize that the formulation and mode of application of an active ingredient, such as a herbicide or safener, or a combination of herbicides or safeners, or a combination thereof, may affect the activity of such material or combination thereof in a given application. Thus, for agricultural use the present herbicides or safeners may be formulated as a granular of relatively large particle size (for example, 3/16 or 1/8 US Mesh), as water-soluble or water-dispersible granules, as powdery dusts, as wettable powders, as emulsifiable concentrates, as solutions, or as any of other known types of agriculturally-useful formulations, depending on the desired mode of application. It is to be understood that the amounts specified in this specification, if presented, are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of a herbicidal compound, or compounds, and 99.0 parts of talc.

Wettable powders are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound, or compounds, and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient, or ingredients, is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Microencapsulated formulations consist of envelopments of small particles of toxicant which without limitation, promote prolonged activity, and reduce mammalian toxicity, volatilization losses, environmental degradation, and soil movement. Microcapsules may be prepared by interfacial or in-situ polymerization by; emulsifying an aqueous phase containing one or more emulsifiers and a water-immiscible phase containing the active ingredient, an isocyanate, and an optional hydrocarbon solvent; agitating the emulsion while adding thereto an aqueous solution of at least one polyfunctional amine; and curing the microcapsules by continuing the agitation while warming. Typical polyfunctional amines include without limitation, ethylenediamine, diethyltriamine, triethylenetetramine, and 1,6-hexanediamine. For application, microcapsules may be diluted in water or other liquid vehicle, and are normally applied as a spray to the area to be treated.

Typical wetting, dispersing or emulsifying agents used in agricultural formulations include without limitation, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile carrier such as water, corn oil, kerosene, propylene glycol, or other suitable solvents.

Still other useful formulations for herbicidal applications include simple solutions of the active ingredient, or ingredients, in a solvent in which they are completely soluble at the desired concentration, such as water, acetone, alkylated naphthalenes, xylene, or other organic solvents.

Granular formulations, wherein the toxicant is carried on coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient, or ingredients, in the range of say 0.1% or 0.2% to 1.5% or 2%.

The following example further illustrates the present invention, but, of course, should not be construed as in any way limiting its scope. The example sets forth certain biological data illustrating the efficacy of the methods of the present invention in safening plants when compared to exposure of the plants to the herbicidal compound alone.

The compounds and compositions of the present invention were tested as water/surfactant solutions on two corn varieties (Pioneer 3733 and Pioneer 3876) and one variety (DPL 61) of cotton. In one embodiment, the safening compound and herbicidal compound were sprayed in admixture as a tank mix onto flats of corn or cotton seeds arranged in a randomized, block design. In another embodiment, the safening compound was applied to the plant seeds by placing the safening compound and the plant seeds in a screw-capped jar, which was rolled on its side until dispersion of the safening compound was complete. Optionally, a sticker compound, for example, without limitation, water or carboxymethylcellulose, can be used to adhere the safening compound to the plant seeds. The treated plant seeds were planted and immediately sprayed with herbicidal compound as described hereinabove. There were four replicates for each rate of application. The emerging corn and cotton plants were maintained in a growth chamber for 14 days after which time they were evaluated for percent injury as compared to an untreated control.

Dietholate Safening of Cotton From The Phytotoxic Effects Of Clomazone

| Rate of Application (kg/ha) | | Percent Injury | Percent Reduction of Injury |
|---|---|---|---|
| Clomazone | Dietholate | | |
| 0.25 | — | 46 | — |
| 0.25 | 0.15 | 27 | 41.3 |
| 0.25 | 0.30 | 27 | 41.3 |
| 0.25 | 0.60 | 23 | 50.0 |
| 0.25 | 0.02–0.05[1] | 19 | 58.7 |
| 0.25 | 0.10–0.2[2] | 9 | 80.0 |
| 0.50 | — | 77 | — |
| 0.50 | 0.15 | 71 | 7.8 |
| 0.50 | 0.30 | 64 | 16.9 |
| 0.50 | 0.60 | 54 | 29.9 |
| 0.50 | 0.02–0.05[1] | 56 | 27.3 |
| 0.50 | 0.10–0.2[2] | 39 | 64.5 |
| 1.0 | — | 91 | — |
| 1.0 | 0.15 | 83 | 8.8 |
| 1.0 | 0.30 | 81 | 11.0 |
| 1.0 | 0.60 | 76 | 16.5 |
| 1.0 | 0.02–0.05[1] | 77 | 15.4 |
| 1.0 | 0.10–0.2[2] | 63 | 30.8 |
| — | — | 0 | 0 |
| — | 0.15 | 0 | 0 |
| — | 0.30 | 0 | 0 |
| — | 0.60 | 0 | 0 |
| — | 0.02–0.05[1] | 0 | 0 |
| — | 0.10–0.2[2] | 1.0 | 0 |

[1]Safening compound applied as a seed treatment at 0.1% wt. of seed.
[2]Safening compound applied as a seed treatment at 0.5% wt. of seed.

Dietholate Safening of Corn From The Phytotoxic Effects Of Clomazone

| Rate of Application (kg/ha) | | Pioneer 3733 | | Pioneer 3876 | |
|---|---|---|---|---|---|
| Clomazone | Dietholate | Percent Injury | Percent Reduction of Injury | Percent Injury | Percent Reduction of Injury |
| 0.06 | — | 2 | — | 1 | — |
| 0.06 | 0.4 | 1 | 50.0 | 1 | 0 |
| 0.06 | 0.8 | 1 | 50.0 | 1 | 0 |
| 0.12 | — | 28 | — | 15 | — |
| 0.12 | 0.4 | 10 | 64.3 | 8 | 46.7 |
| 0.12 | 0.8 | 9 | 67.9 | 8 | 46.7 |
| 0.24 | — | 75 | — | 59 | — |
| 0.24 | 0.4 | 59 | 21.3 | 40 | 32.2 |
| 0.24 | 0.8 | 56 | 25.3 | 37 | 37.3 |
| — | — | 0 | 0 | 0 | 0 |
| — | 0.4 | 0 | 0 | 0 | 0 |
| — | 0.8 | 0 | 0 | 0 | 0 |

As set forth in the forgoing tables, without the safening compound dietholate, the herbicidal compound clomazone caused significant injury to corn and to cotton. Applications of the safening compound dietholate at a rate of, for example, 0.60 kg/ha in admixture with herbicidal compound clomazone at a rate of, for example, 0.25 kg/ha, reduced the injury to cotton by about 50%. When safening compound dietholate is applied to cotton seeds as a seed treatment at a rate of, for example, from about 0.1 kg/ha to 0.2 kg/ha, followed by application of the herbicidal compound clomazone at a rate of, for example, 0.25 kg/ha, the injury to cotton is reduced by about 80%.

Applications of the safening compound dietholate at a rate of, for example, 0.80 kg/ha in admixture with herbicidal compound clomazone at a rate of, for example, 0.12 kg/ha, reduced the injury to the two varieties of corn in the test by an average of about 57.3%. While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of protecting a plant from unintentional phytotoxic injury from application of a herbicidally-effective amount of a herbicidal compound to the locus of said plant, which method comprises applying to said locus an effective amount of one or more safening compounds having formula (I):

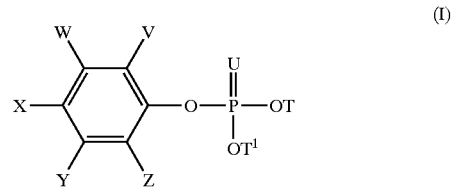

(I)

wherein
T and T$^1$ are independently selected from the group of hydrogen, alkyl, haloalkyl, alkoxyalkyl, alkenyl, and alkynyl;
U is O or S, and;
V, W, X, Y, and Z are independently selected from the group of hydrogen, halogen, alkyl, haloalkyl, and alkoxy; and, wherein
said herbicidal compound is a 3-isoxazolidinone having formula (II):

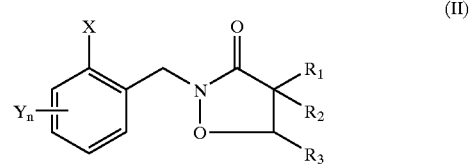

(II)

wherein:

R₁ and R₂ are independently selected from $C_1$–$C_4$ alkyl;

R₃ is hydrogen, halogen, phenylamino, or —OR₄ in which R₄ is hydrogen, lower alkyl, alkenyl, alkynyl, alkoxyalkyl up to 6 carbons, phenylmethyl, $C_2$–$C_4$ acyl, haloacyl, phenylacyl, alkylcarbonylamino, or phenylcarbonylamino;

X is hydrogen, lower alkyl, or halogen;

Y is halogen, cyano, $C_1$–$C_4$ alkoxy, or 4,5-methylenedioxy, and;

n is 0, 1, or 2.

2. The method according to claim 1, wherein R₁ and R₂ are methyl, R₃ is hydrogen, X is chlorine, and n is 0.

3. The method according to claim 1, wherein T and T¹ are ethyl, U is sulfur, and; V, W, X, Y, and Z are hydrogen.

4. The method according to claim 1, wherein said plant is selected from the group of soybean, cotton, sugarbeet, rape (canola), potato, sunflower, peanut, lettuce, carrot, sweet potato, alfalfa, tobacco, corn (maize), rice, sorghum, wheat, barley, oats, rye, triticale, and sugarcane.

5. The method according to claim 4, wherein said plant is wheat, corn or cotton.

6. The method according to claim 5, wherein said plant is cotton, said herbicidal compound is clomazone, and said safening compound is dietholate.

7. The method according to claim 1, wherein said herbicidal compound is applied to the locus of said plant in an amount of about 0.001 to about 15 kilograms/hectare and said safening compound in an amount of about 0.003 to about 15 kilograms/hectare.

8. The method according to claim 7, wherein said amount of said herbicidal compound is from about 0.003 to about 5 kilograms/hectare and said amount of said safening compound is from about 0.01 to about 5 kilograms/hectare.

9. The method according to claim 1, wherein said safening compound and said herbicide are applied as a seed treatment of a seed of a said plant.

10. The method according to claim 9, wherein said safening compound comprises from about 0.005 weight percent to about 10 weight percent of said treated seed.

11. The method according to claim 1, wherein said safening compound is combined with an agriculturally acceptable carrier.

12. An agricultural chemical composition, comprising a herbicidally effective amount of a herbicidal compound and a safening compound as claimed in claim 1.

13. The agricultural chemical composition of claim 12, further comprising an agriculturally acceptable carrier.

14. The agricultural chemical composition of claim 12, wherein the safening compound is dietholate.

15. The agricultural chemical composition of claim 14, wherein the herbicidal compound is clomazone.

16. The method according to claim 9, wherein said plant seed is cotton, said herbicide is clomazone, and said safening compound applied as a seed treatment is dietholate.

* * * * *